United States Patent
Libbus et al.

(10) Patent No.: US 12,350,496 B2
(45) Date of Patent: *Jul. 8, 2025

(54) IMPLANTABLE NEUROSTIMULATOR-IMPLEMENTED METHOD FOR MANAGING BRADYCARDIA THROUGH VAGUS NERVE STIMULATION

(71) Applicant: LivaNova USA, Inc., Houston, TX (US)

(72) Inventors: Imad Libbus, St. Paul, MN (US); Badri Amurthur, Los Gatos, CA (US); Bruce H. KenKnight, Maple Grove, MN (US)

(73) Assignee: LivaNova USA, Inc., Houston, TX (US)

( * ) Notice: Subject to any disclaimer, the term of this patent is extended or adjusted under 35 U.S.C. 154(b) by 484 days.

This patent is subject to a terminal disclaimer.

(21) Appl. No.: 17/486,188

(22) Filed: Sep. 27, 2021

(65) Prior Publication Data

US 2022/0118250 A1 Apr. 21, 2022

Related U.S. Application Data

(63) Continuation of application No. 15/922,863, filed on Mar. 15, 2018, now Pat. No. 11,129,992, which is a
(Continued)

(51) Int. Cl.
*A61N 1/365* (2006.01)
*A61B 5/363* (2021.01)
*A61N 1/36* (2006.01)

(52) U.S. Cl.
CPC ............. *A61N 1/365* (2013.01); *A61B 5/363* (2021.01); *A61N 1/36114* (2013.01);
(Continued)

(58) Field of Classification Search
None
See application file for complete search history.

(56) References Cited

U.S. PATENT DOCUMENTS 8,688,212 B2 * 4/2014 Libbus ............... A61N 1/36114
607/18
9,919,157 B2 * 3/2018 Libbus ................... A61B 5/363
(Continued)

OTHER PUBLICATIONS

International Search Report for PCT Application No. PCT/US2013/050390, mail date Nov. 5, 2013, 6 pages.
(Continued)

*Primary Examiner* — William J Levicky
*Assistant Examiner* — Willow Grace Welch
(74) *Attorney, Agent, or Firm* — Foley & Lardner LLP

(57) ABSTRACT

A method for managing bradycardia through vagus nerve stimulation is provided. An implantable neurostimulator configured to deliver electrical therapeutic stimulation in both afferent and efferent directions of a patient's cervical vagus nerve is provided. An operating mode is stored, which includes parametrically defining a maintenance dose of the electrical therapeutic stimulation tuned to restore cardiac autonomic balance through continuously-cycling, intermittent and periodic electrical pulses. The maintenance dose is delivered via a pulse generator through a pair of helical electrodes via an electrically coupled nerve stimulation therapy lead independent of cardiac cycle. The patient's physiology is monitored, and upon sensing a condition indicative of bradycardia, the delivery of the maintenance dose is suspended. A progressively increasing amount of time is spent waiting via a controller and, upon sensing a condition indicative of an absence or termination of the bradycardia, a progressively increasing partial maintenance dose is delivered via the pulse generator.

18 Claims, 6 Drawing Sheets

Related U.S. Application Data continuation of application No. 14/177,542, filed on Feb. 11, 2014, now Pat. No. 9,919,157, which is a continuation of application No. 13/554,656, filed on Jul. 20, 2012, now Pat. No. 8,688,212.

(52) U.S. Cl.
CPC ..... *A61N 1/36139* (2013.01); *A61N 1/36167* (2013.01); *A61N 1/36175* (2013.01); *A61N 1/36171* (2013.01)

(56) References Cited

U.S. PATENT DOCUMENTS

| | | | | |
|---|---|---|---|---|
| 11,129,992 | B2 * | 9/2021 | Libbus | A61N 1/36167 |
| 2003/0216790 | A1 * | 11/2003 | Hill | A61N 1/36114 607/17 |
| 2005/0197675 | A1 * | 9/2005 | David | A61B 5/412 607/9 |
| 2006/0271108 | A1 * | 11/2006 | Libbus | A61N 1/36114 607/2 |
| 2008/0086181 | A1 * | 4/2008 | Amurthur | A61N 1/36114 607/45 |
| 2010/0010556 | A1 | 1/2010 | Zhao et al. | |
| 2010/0114197 | A1 | 5/2010 | Burnes et al. | |
| 2012/0303080 | A1 * | 11/2012 | Ben-David | A61N 1/36114 607/119 |
| 2012/0330373 | A1 * | 12/2012 | Ternes | A61N 1/36167 607/42 |
| 2013/0158616 | A1 | 6/2013 | Libbus et al. | |
| 2013/0158617 | A1 | 6/2013 | Libbus et al. | |

OTHER PUBLICATIONS

Office Action on European Patent Application No. 13741950.3 dated Apr. 17, 2018. 5 pages.

\* cited by examiner

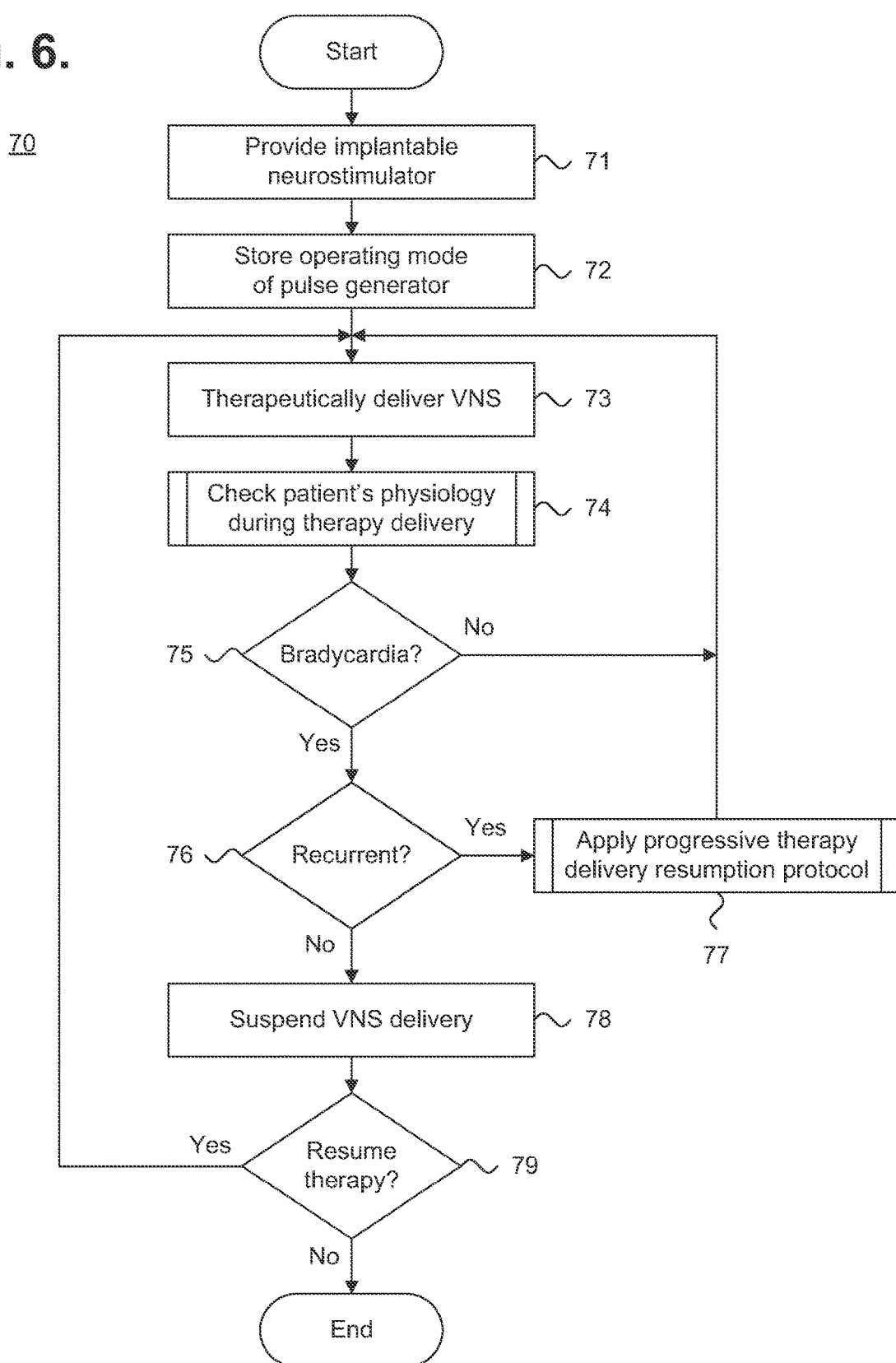

90

80

IMPLANTABLE NEUROSTIMULATOR-IMPLEMENTED METHOD FOR MANAGING BRADYCARDIA THROUGH VAGUS NERVE STIMULATION

CROSS REFERENCE TO RELATED APPLICATIONS

This application is a continuation of U.S. patent application Ser. No. 15/922,863, filed Mar. 15, 2018, which is a continuation of U.S. patent application Ser. No. 14/177,542, filed Feb. 11, 2014, now U.S. Pat. No. 9,919,157, which is a continuation of U.S. patent application Ser. No. 13/554,656, filed Jul. 20, 2012, now U.S. Pat. No. 8,688,212, the disclosures of all are incorporated by reference herein in their entirety.

FIELD

This application relates in general to chronic cardiac dysfunction therapy and, in particular, to an implantable neurostimulator-implemented method for managing bradycardia through vagus nerve stimulation.

BACKGROUND

Congestive heart failure (CHF) is a progressive and physically debilitating chronic condition in which the heart is unable to supply sufficient blood flow to meet the body's needs. Pathologically, CHF is characterized by an elevated neuroexitatory state accompanied by impaired arterial and cardiopulmonary baroreflex function and reduced vagal activity. CHF is initiated by cardiac dysfunction, which triggers compensatory activations of the sympathoadrenal (sympathetic) nervous and the renin-angiotensin-aldosterone hormonal systems. Initially, these mechanisms help the heart compensate for deteriorating pumping function, yet over time, overdriven sympathetic activation and increased heart rate promote progressive left ventricular dysfunction and deleterious remodeling.

Sympathetic nervous system activation also significantly increases the risk and severity of bradycardia. Parasympathetic activity generally dominates over sympathetic activity. Consequently, increases in parasympathetic activity due to the triggering of CHF compensatory mechanisms can evoke pronounced bradycardia in light of the already high level of sympathetic activity stemming from chronic cardiac dysfunction. Pathologic bradycardia are categorized as either atrial, atrioventricular or ventricular, based upon the level of disturbance to normal impulse generation and conduction. Sick sinus bradycardia, a form of atrial bradycardia, is caused by sinus node malfunction. Atrioventricular nodal bradycardia occurs due to an absence of electrical impulse from the sinus node. Ventricular bradycardia occurs as the result of atrioventricular block due to an impairment in impulse conduction.

Chronic cardiac dysfunction stems from an autonomic imbalance of the sympathetic and parasympathetic nervous systems that, if left untreated, leads to cardiac arrhythmogenesis, including bradycardia, progressively worsening cardiac function and eventual death. The current standard of care for managing chronic cardiac dysfunction mandates prescription of pharmacological agents, including diuretics, angiotensin-converting enzyme inhibitors, angiotensin receptor blockers, beta-blockers, and aldosterone antagonists, and dietary and lifestyle changes. However, the effectiveness of these measures is only palliative, not curative, and patients often suffer side effects and comorbidities due to disease progression, such as pulmonary edema, sleep apnea, and myocardial ischemia.

Cardiac resynchronization therapy (CRT) has recently become available to those chronic cardiac dysfunction patients with impaired systolic function. CRT restores synchronous heartbeat through coordinated bi-ventricular pacing that helps improve contractile cardiac performance. However, CRT only addresses systolic dysfunction and is limited to patients exhibiting a wide QRS complex (mechanical dyssynchrony) and reduced left ventricular ejection fraction.

Neural stimulation has been proposed as a complementary treatment for chronic cardiac dysfunction that directly addresses the underlying autonomic nervous system imbalance, rather than relieving symptoms or directly pacing heart muscle. Activity within and among elements of both sympathetic and parasympathetic nervous systems regulate cardiovascular function by exerting high resolution control over key biological processes mediated by ionic currents flowing across cell membranes. Cumulatively, in a healthy person, the autonomic regulation of these biological processes results in stable homeostasis of heart rate and normal contractile performance. However, when disease processes derange autonomic function, homeostasis is lost and cardiovascular function is degraded; contractile performance thus becomes suboptimal and heart rate modulation is distorted in ways that create a positive feedback loop that promotes progression of chronic cardiac dysfunction and ultimately risks CHF. Neural stimulation can break the positive feedback loop through the suppression of excessive neural activation by electrically modulating select vagus nerve fibers. The electrical modulation may help improve cardiac mechanical function and reduce the heart's intrinsic nervous system's propensity to induce atrial and ventricular arrhythmias, including bradycardia, during chronic autonomic nervous system imbalance.

Notwithstanding, vagus nerve stimulation (VNS) is currently only approved for the clinical treatment of drug-refractory epilepsy and depression, although VNS has been proposed as a long-term therapeutic treatment of CHF. Conventional therapeutic alteration of cardiac vagal efferent activation through electrical stimulation targets only the efferent nerves of the parasympathetic nervous system and is clinically insufficient to restore autonomic balance. Any therapeutic effect on parasympathetic activation clinically occurs as a result of incidental recruitment of afferent parasympathetic nerve fibers and not as an intended and desired outcome of the efferent-centric neurostimulation, such as described in Sabbah et al., "Vagus Nerve Stimulation in Experimental Heart Failure," Heart Fail. Rev., 16:171-178 (2011), the disclosure of which is incorporated by reference. The Sabbah paper discusses canine studies using a vagus stimulation device, manufactured by BioControl Medical Ltd., Yehud, Israel, which includes a signal generator, right ventricular endocardial sensing lead, and right vagus nerve cuff stimulation lead. The sensing leads enable stimulation of the right vagus nerve to be synchronized to the cardiac cycle through closed-loop heart rate control. A bipolar nerve cuff electrode is surgically implanted on the right vagus nerve at the mid-cervical position. An asymmetric bi-polar multi-contact cuff electrode provides cathodic induction of action potentials while simultaneously applying asymmetric anodal blocks that lead to preferential, but not exclusive, activation of vagal efferent fibers. Electrical stimulation of the right cervical vagus nerve is delivered only when heart rate increases beyond a preset threshold. Stimulation is provided at an impulse rate and intensity intended to reduce basal heart rate by ten percent by preferential stimulation of efferent vagus nerve fibers leading to the heart while blocking afferent neural impulses to the brain. Although effective in restoring baroreflex sensitivity and, in the canine model, increasing left ventricular ejection fraction and decreasing left ventricular end diastolic and end systolic volumes, restoration of autonomic balance was not addressed.

Other uses of electrical nerve stimulation for therapeutic treatment of various physiological conditions are described. For instance, U.S. Pat. No. 6,600,954, issued Jul. 29, 2003 to Cohen et al. discloses a method and apparatus for selective control of nerve fibers. An electrode device is applied to a nerve bundle capable of generating, upon activation, unidirectional action potentials to be propagated through both small diameter and large diameter sensory fibers in the nerve bundle, and away from the central nervous system. The device is particularly useful for reducing pain sensations in the legs and arms.

U.S. Pat. No. 6,684,105, issued Jan. 27, 2004 to Cohen et al. discloses an apparatus for treatment of disorders by unidirectional nerve stimulation. An apparatus for treating a specific condition includes a set of one or more electrode devices that are applied to selected sites of the central or peripheral nervous system of the patient. For some applications, a signal is applied to a nerve, such as the vagus nerve, to stimulate efferent fibers and treat motility disorders, or to a portion of the vagus nerve innervating the stomach to produce a sensation of satiety or hunger. For other applications, a signal is applied to the vagus nerve to modulate electrical activity in the brain and rouse a comatose patient, or to treat epilepsy and involuntary movement disorders.

U.S. Pat. No. 7,123,961, issued Oct. 17, 2006 to Kroll et al. discloses stimulation of autonomic nerves. An autonomic nerve is stimulated to affect cardiac function using a stimulation device in electrical communication with the heart by way of three leads suitable for delivering multi-chamber stimulation and shock therapy. In addition, the device includes a fourth lead having three electrodes positioned in or near the heart, or near an autonomic nerve remote from the heart. Power is delivered to the electrodes at a set power level. The power is delivered at a reduced level if cardiac function was affected.

U.S. Pat. No. 7,225,017, issued May 29, 2007 to Shelchuk discloses terminating ventricular tachycardia in connection with any stimulation device that is configured or configurable to stimulate nerves, or stimulate and shock a patient's heart. Parasympathetic stimulation is used to augment anti-tachycardia pacing, cardioversion, or defibrillation therapy. To sense atrial or ventricular cardiac signals and provide chamber pacing therapy, particularly on the left side of the patient's heart, the stimulation device is coupled to a lead designed for placement in the coronary sinus or its tributary veins. Cardioversion stimulation is delivered to a parasympathetic pathway upon detecting a ventricular tachycardia. A stimulation pulse is delivered via the lead to one or more electrodes positioned proximate to the parasympathetic pathway according to stimulation pulse parameters based at least in part on the probability of reinitiation of an arrhythmia. In a further embodiment, the stimulation pulse is delivered post inspiration or during a refractory period to cause a release of acetylcholine. The stimulation device can further include a "rate-responsive" physiologic sensor to adjust pacing stimulation rate according to the exercise state of the patient or in response to changes in cardiac output.

U.S. Pat. No. 7,277,761, issued Oct. 2, 2007 to Shelchuk discloses vagal stimulation for improving cardiac function in heart failure or CHF patients. An autonomic nerve is stimulated to affect cardiac function using a stimulation device in electrical communication with the heart by way of three leads suitable for delivering multi-chamber endocardial stimulation and shock therapy. In addition, the device includes a fourth lead having three electrodes positioned in or near the heart, or near an autonomic nerve remote from the heart. A need for increased cardiac output is detected through the lead and a stimulation pulse is delivered proximate to the left vagosympathetic trunk or branch to thereby stimulate a parasympathetic nerve. If the stimulation has caused sufficient increase in cardiac output, ventricular pacing may then be initiated at an appropriately reduced rate.

U.S. Pat. No. 7,295,881, issued Nov. 13, 2007 to Cohen et al. discloses nerve branch-specific action potential activation, inhibition and monitoring. Two preferably unidirectional electrode configurations flank a nerve junction from which a preselected nerve branch issues, proximally and distally to the junction, with respect to the brain. Selective nerve branch stimulation can be used in conjunction with nerve-branch specific stimulation to achieve selective stimulation of a specific range of fiber diameters, substantially restricted to a preselected nerve branch, including heart rate control, where activating only the vagal B nerve fibers in the heart, and not vagal A nerve fibers that innervate other muscles, can be desirous.

U.S. Pat. No. 7,778,703, issued Aug. 17, 2010 to Gross et al. discloses selective nerve fiber stimulation for treating heart conditions. An electrode device is adapted to be coupled to a vagus nerve of a subject and a control unit drives the electrode device by applying stimulating and inhibiting currents to the vagus nerve, which are capable of respectively inducing action potentials in a therapeutic direction in a first set and a second set of nerve fibers in the vagus nerve and inhibiting action potentials in the therapeutic direction in the second set of nerve fibers only. The nerve fibers in the second set have larger diameters than the nerve fibers in the first set. The control unit typically drives the electrode device to apply signals to the vagus nerve to induce the propagation of efferent action potentials towards the heart and suppress artificially-induced afferent action potentials toward the brain. Patient control is not mentioned.

U.S. Pat. No. 7,813,805, issued Oct. 12, 2010 to Farazi and U.S. Pat. No. 7,869,869, issued Jan. 11, 2011 to Farazi both disclose subcardiac threshold vagus nerve stimulation. A vagus nerve stimulator is configured to generate electrical pulses below a cardiac threshold, which are transmitted to a vagus nerve, so as to inhibit or reduce injury resulting from ischemia. The cardiac threshold is a threshold for energy delivered to the heart above which there is a slowing of the heart rate or conduction velocity. In operation, the vagus nerve stimulator generates the electrical pulses below the cardiac threshold, such that heart rate is not affected. Patient control is also not mentioned.

Finally, U.S. Pat. No. 7,885,709, issued Feb. 8, 2011 to Ben-David discloses nerve stimulation for treating disorders. A control unit drives an electrode device to stimulate the vagus nerve, so as to modify heart rate variability, or to reduce heart rate, by suppressing the adrenergic (sympathetic) system. The vagus stimulation reduces the release of catecholamines in the heart, thus lowering adrenergic tone at its source. For some applications, the control unit synchronizes the stimulation with the cardiac cycle, while for other applications, the stimulation can be applied, for example, in a series of pulses. To reduce heart rate, stimulation is applied using a target heart rate lower than the subject's normal average heart rate. In one embodiment, the control unit is further adapted to detect bradycardia and to terminate heart rate regulation immediately upon such detection, such as by ceasing vagus stimulation of the sympathetic nervous system. Additionally, the control unit can use an algorithm that reacts to regulate heart rate when the heart rate crosses limits that are predefined, for instance, a low limit of 40 bpm and a high limit of 140 bpm, or as determined in real time, such as responsive to sensed physiological values.

Accordingly, a need remains for an approach to therapeutically treating chronic cardiac dysfunction, including CHF, and cardiac arrhythmogenesis, specifically bradycardia, through a form of VNS to restore autonomic balance.

SUMMARY

Excessive sustained activation of the sympathetic nervous system has a deleterious effect on long term cardiac performance and increases the risk of bradycardia and related forms of arrhythmia. Bi-directional afferent and efferent neural stimulation through the vagus nerve can beneficially restore autonomic balance and improve long term patient outcome. The neural stimulation is provided in a low level maintenance dose independent of cardiac cycle. VNS delivery can be provided through an implantable vagus neurostimulator and electrode lead, which suspends delivery of the maintenance dose upon sensing a condition indicative of bradycardia. VNS delivery is only continually resumed if, during post-suspension monitoring, bradycardia is not found to recur as a result of VNS resumption.

One embodiment provides an implantable neurostimulator and implantable neurostimulator-implemented method for managing bradycardia through vagus nerve stimulation. An operating mode of the implantable neurostimulator is stored, which includes parametrically defining a maintenance dose of the electrical therapeutic stimulation tuned to restore cardiac autonomic balance through continuously-cycling, intermittent and periodic electrical pulses. The maintenance dose is therapeutically delivered to the vagus nerve via a pulse generator included in the neurostimulator through a pair of helical electrodes via an electrically coupled nerve stimulation therapy lead independent of cardiac cycle. The patient's physiology is monitored via a physiological sensor included in the implantable neurostimulator, and upon sensing a condition indicative of bradycardia, the delivery of the maintenance dose by the pulse generator to the vagus nerve is suspended. A progressively increasing amount of time is spent waiting via a controller included in the implantable neurostimulator and, upon sensing a condition indicative of an absence or termination of the bradycardia, a progressively increasing partial maintenance dose is delivered to the vagus nerve via the pulse generator.

A further embodiment provides an implantable neurostimulator and implantable neurostimulator-implemented method for managing bradycardia through vagus nerve stimulation. A maintenance dose of electrical therapeutic stimulation for delivery via an implantable neurostimulator is defined and tuned to restore cardiac autonomic balance through continuously-cycling, intermittent and periodic electrical pulses. The maintenance dose is delivered to the vagus nerve through a pair of helical electrodes via a stimulation therapy lead electrically coupled nerve to a pulse generator included in the implantable neurostimulator. The maintenance dose is therapeutically delivered via the pulse generator to the vagus nerve in both afferent and efferent directions of a cervical vagus nerve of a patient independent of cardiac cycle. The patient's physiology is periodically monitored via a physiological sensor included in the implantable neurostimulator. Upon sensing a condition indicative of bradycardia, the delivery of the maintenance dose to the vagus nerve is suspended. A back-off delay including an amount of time that increases over each previous back-off delay is determined via a controller included in the implantable neurostimulator. Upon expiry of the back-off delay, the patient's physiology is checked via the physiological sensor. Upon sensing a condition indicative of an absence or termination of the bradycardia, the maintenance dose is delivered at a partial duty cycle to the vagus nerve via the pulse generator. The monitoring of the patient's physiology is resumed via the physiological sensor. Upon sensing a condition indicative of a continued absence of bradycardia, the duty cycle of the maintenance dose is gradually increased.

By restoring autonomic balance, therapeutic VNS operates acutely to decrease heart rate, increase heart rate variability and coronary flow, reduce cardiac workload through vasodilation, and improve left ventricular relaxation without aggravating comorbid bradycardia or other cardiac arrhythmic conditions. Over the long term, low dosage VNS provides the chronic benefits of decreased negative cytokine production, increased baroreflex sensitivity, increased respiratory gas exchange efficiency, favorable gene expression, renin-angiotensin-aldosterone system down-regulation, and anti-arrhythmic, anti-apoptotic, and ectopy-reducing anti-inflammatory effects.

Still other embodiments of the present invention will become readily apparent to those skilled in the art from the following detailed description, wherein are described embodiments by way of illustrating the best mode contemplated for carrying out the invention. As will be realized, the invention is capable of other and different embodiments and its several details are capable of modifications in various obvious respects, all without departing from the spirit and the scope of the present invention. Accordingly, the drawings and detailed description are to be regarded as illustrative in nature and not as restrictive.

BRIEF DESCRIPTION OF THE DRAWINGS

FIG. 6 is a flow diagram showing an implantable neurostimulator-implemented method for managing bradycardia through vagus nerve stimulation, in accordance with one embodiment.

DETAILED DESCRIPTION

Functional behavior of heart tissue is influenced by the autonomic nervous system, which plays a key pathogenic role in the cause of and the biological response to cardiovascular disease. Complex changes in autonomic control of the cardiovascular systems of patients suffering from a cardiovascular disease push the autonomic nervous system out of balance and favor increased sympathetic and decreased parasympathetic central outflow. The imbalance is accompanied by pronounced bradycardia due to the elevated parasympathetic activity triggered to respond to the compensatory sympathetic activity. Peripheral neurostimulation therapies that target the imbalance of the autonomic nervous system found in individuals with severe CHF have been shown to improve outcomes. Specifically, propagating efferent and afferent action potentials through bi-directional autonomic regulation therapy activates both parasympathetic afferent and efferent nerve fibers in the vagus nerve simultaneously. The therapy directly restores autonomic balance by engaging both medullary and cardiac reflex control components of the autonomic nervous system. Upon stimulation of the cervical vagus nerve, action potentials propagate away from the stimulation site in two directions, efferently toward the heart and afferently toward the brain. Efferent action potentials influence the intrinsic cardiac nervous system and the heart, while afferent action potentials influence central elements of the nervous system.

Figure 1:
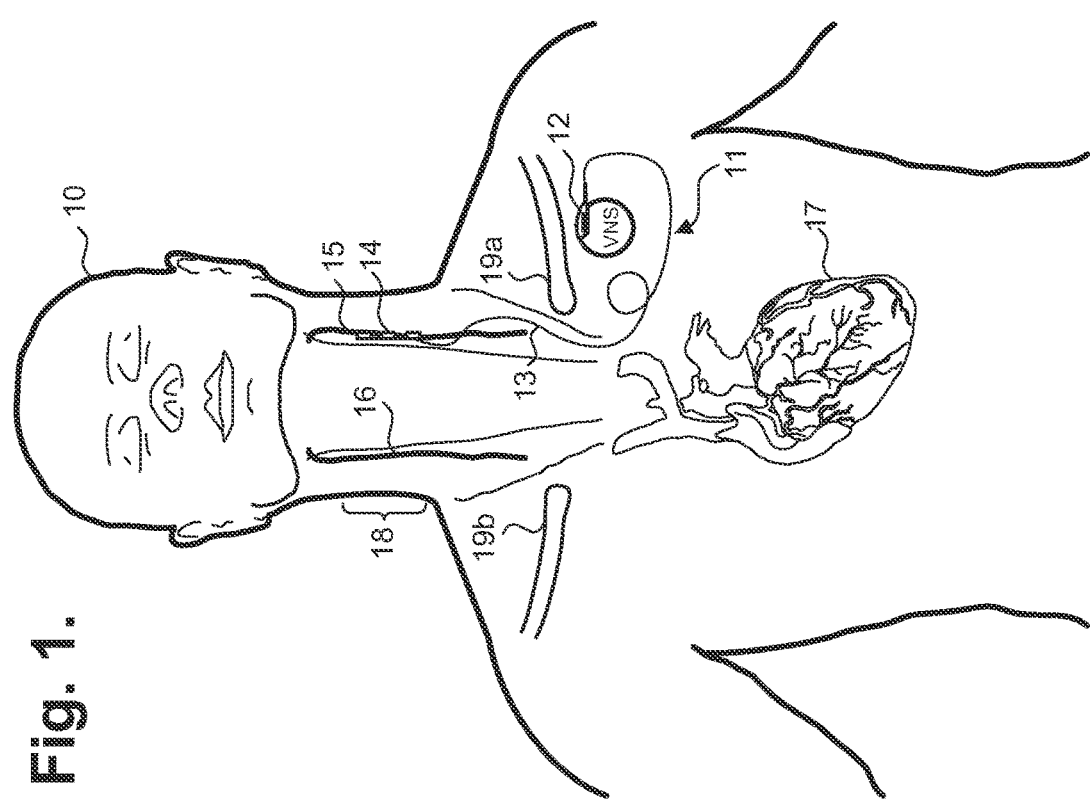
FIG. 1 is a front anatomical diagram showing, by way of example, placement of an implantable vagus stimulation device in a male patient, in accordance with one embodiment.

An implantable vagus nerve stimulator, such as used to treat drug-refractory epilepsy and depression, can be adapted for use in managing chronic cardiac dysfunction through therapeutic bi-directional vagal stimulation. FIG. 1 is a front anatomical diagram showing, by way of example, placement of an implantable vagus stimulation device 11 in a male patient 10, in accordance with one embodiment. The VNS provided through the stimulation device 11 operates under several mechanisms of action. These mechanisms include increasing parasympathetic outflow and inhibiting sympathetic effects by blocking norepinephrine release. More importantly, VNS triggers the release of acetylcholine (ACh) into the synaptic cleft, which has beneficial anti-arrhythmic, anti-apoptotic, and ectopy-reducing anti-inflammatory effects.

The implantable vagus stimulation device 11 includes at least three implanted components, an implantable neurostimulator 12, a therapy lead 13, and helical electrodes 14. The implantable vagus stimulation device 11 can be remotely accessed following implant through an external programmer by which the neurostimulator 12 can be remotely checked and programmed by healthcare professionals; an external magnet, such as described in commonly-assigned U.S. Patent application, entitled "Implantable Device For Facilitating Control Of Electrical Stimulation Of Cervical Vagus Nerves For Treatment Of Chronic Cardiac Dysfunction," Ser. No. 13/314,130, filed on Dec. 7, 2011, pending, the disclosure of which is incorporated by reference, for basic patient control; and an electromagnetic controller, such as described in commonly-assigned U.S. Patent application, entitled "Vagus Nerve Neurostimulator With Multiple Patient-Selectable Modes For Treating Chronic Cardiac Dysfunction," Ser. No. 13/352,244, filed on Jan. 17, 2012, pending, the disclosure of which is incorporated by reference, that enables the patient 10 to exercise increased control over therapy delivery and suspension. Together, the implantable vagus stimulation device 11 and one or more of the external components form a VNS therapeutic delivery system.

The neurostimulator 12 is implanted in the patient's right or left pectoral region generally on the same side (ipsilateral) of the patient's body as the vagus nerve 15, 16 to be stimulated, although other neurostimulator-vagus nerve configurations, including contra-lateral and bi-lateral are possible. The helical electrodes 14 are generally implanted on the vagus nerve 15, 16 about halfway between the clavicle 19a-b and the mastoid process. The therapy lead 13 and helical electrodes 14 are implanted by first exposing the carotid sheath and chosen vagus nerve 15, 16 through a latero-cervical incision on the ipsilateral side of the patient's neck 18. The helical electrodes 14 are then placed onto the exposed nerve sheath and tethered. A subcutaneous tunnel is formed between the respective implantation sites of the neurostimulator 12 and helical electrodes 14, through which the therapy lead 13 is guided to the neurostimulator 12 and securely connected.

The stimulation device 11 bi-directionally stimulates the vagus nerve 15, 16 through application of continuously-cycling, intermittent and periodic electrical stimuli, which are parametrically defined through stored stimulation parameters and timing cycles. In one embodiment, the autonomic regulation therapy is provided in a low level maintenance dose independent of cardiac cycle to activate both parasympathetic afferent and efferent nerve fibers in the vagus nerve simultaneously. Both sympathetic and parasympathetic nerve fibers are stimulated through the helical electrodes 14 of the stimulation device 11. Stimulation of the cervical vagus nerve results in propagation of action potentials in both afferent and efferent directions from the site of stimulation to restore autonomic balance. Afferent action potentials propagate toward the parasympathetic nervous system's origin in the medulla in the nucleus ambiguus, nucleus tractus solitarius, and the dorsal motor nucleus, as well as towards the sympathetic nervous system's origin in the intermediolateral cell column of the spinal cord. Efferent action potentials propagate toward the heart 17 to activate the components of the heart's intrinsic nervous system. Either the left or right vagus nerve 15, 16 can be stimulated by the stimulation device 11, although stimulation of the right vagus nerve 16 has a moderately stronger affect on heart rate (on the order of approximately 20% stronger) than left vagus nerve 15 stimulation at the same parametric levels.

Figure 2B:
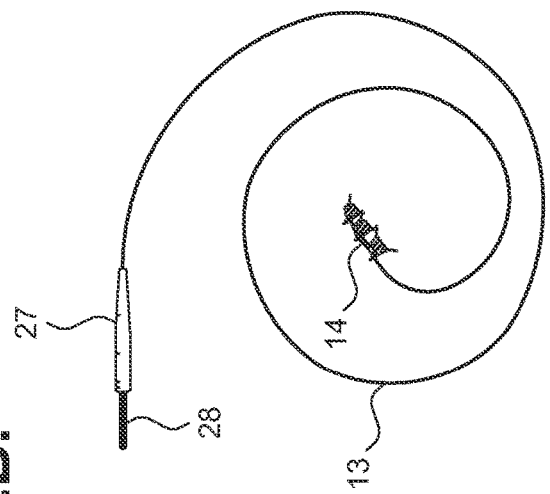
FIGS. 2A and 2B are diagrams respectively showing the implantable neurostimulator and the simulation therapy lead of FIG. 1.
Figure 2A:
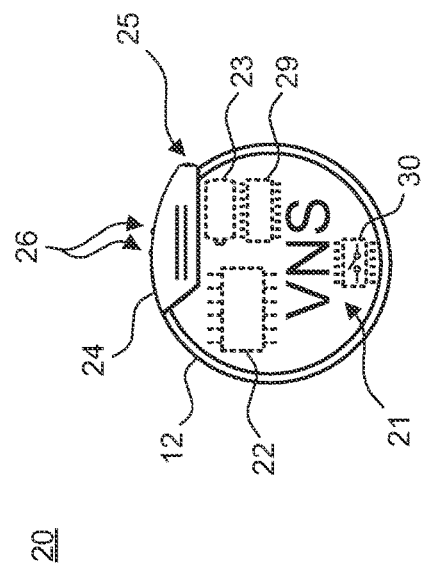

The VNS therapy is autonomously delivered to the patient's vagus nerve 15, 16 through three implanted components that include a neurostimulator 12, therapy lead 13, and helical electrodes 14. FIGS. 2A and 2B are diagrams respectively showing the implantable neurostimulator 12 and the simulation therapy lead 13 of FIG. 1. In one embodiment, the neurostimulator 12 can be adapted from a VNS Therapy AspireHC Model 105 pulse generator or a VNS Therapy AspireSR Model 106 pulse generator, both manufactured and sold by Cyberonics, Inc., Houston, TX, although other manufactures and types of single-pin receptacle implantable VNS neurostimulators could also be used.

The stimulation therapy lead 13 and helical electrodes 14 are generally fabricated as a combined assembly and can be adapted from a Model 302 lead, PerenniaDURA Model 303 lead, or PerenniaFLEX Model 304 lead, also manufactured and sold by Cyberonics, Inc., in two sizes based on helical electrode inner diameter, although other manufactures and types of single-pin receptacle-compatible therapy leads and electrodes could also be used.

Referring first to FIG. 2A, the neurostimulator 12 provides continuously-cycling, intermittent and periodic ON-OFF cycles of vagal stimulation in a maintenance does that when, applied to the vagus nerve through the electrodes 14, produce action potentials in the underlying nerves that propagate bi-directionally. Afferently propagating action potentials activate the medial medullary sites responsible for central reflex control and efferently propagating action potentials activate both the heart's intrinsic nervous system and the heart directly. The neurostimulator 12 includes an electrical pulse generator that is tuned to restore autonomic balance by triggering action potentials that propagate both afferently and efferently within the vagus nerve 15, 16. The neurostimulator 12 is enclosed in a hermetically sealed housing 21 constructed of a biocompatible, implantation-safe material, such as titanium. The housing 21 contains electronic circuitry 22 powered by a primary battery 22, such as a lithium carbon monoflouride battery. The electronic circuitry 22 is implemented using complementary metal oxide semiconductor integrated circuits that include a microprocessor controller that executes a control program according to stored stimulation parameters and timing cycles; a voltage regulator that regulates system power; logic and control circuitry, including a recordable memory 29 within which the stimulation parameters are stored, that controls overall pulse generator function, receives and implements programming commands from the external programmer, or other external source, and collects and stores telemetry information; a transceiver that remotely communicates with the external programmer using radio frequency signals; an antenna, which receives programming instructions and transmits the telemetry information to the external programmer; and a reed switch 30 that provides remote access to the operation of the neurostimulator 12 using an external programmer, a simple patient magnet, or an electromagnetic controller. The recordable memory 29 can include both volatile (dynamic) and persistent (static) forms of memory, such as firmware within which the stimulation parameters and timing cycles can be stored. Other electronic circuitry and components, such as an integrated heart rate sensor, are possible.

Externally, the neurostimulator 12 includes a header 24 to securely receive and connect to the therapy lead 13. In one embodiment, the header 24 encloses a receptacle 25 into which a single pin for the therapy lead 13 can be received, although two or more receptacles could also be provided, along with the requisite additional electronic circuitry 22. The header 24 internally includes a lead connector block (not shown) and a set of set screws 26.

The neurostimulator 12 is preferably interrogated prior to implantation and throughout the therapeutic period with a healthcare provider-operable external programmer and programming wand (not shown) for checking proper operation, downloading recorded data, diagnosing problems, and programming operational parameters. Generally, use of the external programmer is restricted to healthcare providers, while more limited manual control is provided to the patient through "magnet mode." In one embodiment, the external programmer executes application software specially designed to interrogate the neurostimulator 12. The programming computer interfaces to the programming wand through a standardized wired or wireless data connection. The programming wand can be adapted from a Model 201 Programming Wand, manufactured and sold by Cyberonics, Inc. and the application software can be adapted from the Model 250 Programming Software suite, licensed by Cyberonics, Inc. Other configurations and combinations of external programmer, programming wand and application software are possible.

The neurostimulator 12 delivers VNS under control of the electronic circuitry 22. The stored stimulation parameters are programmable. Each stimulation parameter can be independently programmed to define the characteristics of the cycles of therapeutic stimulation and inhibition to ensure optimal stimulation for a patient 10. The programmable stimulation parameters include output current, signal frequency, pulse width, signal ON time, signal OFF time, magnet activation (for VNS specifically triggered by "magnet mode"), and reset parameters. Other programmable parameters are possible. In addition, sets or "profiles" of preselected stimulation parameters can be provided to physicians with the external programmer and fine-tuned to a patient's physiological requirements prior to being programmed into the neurostimulator 12, such as described in commonly-assigned U.S. Patent application, entitled "Computer-Implemented System and Method for Selecting Therapy Profiles of Electrical Stimulation of Cervical Vagus Nerves for Treatment of Chronic Cardiac Dysfunction," Ser. No. 13/314,138, filed on Dec. 7, 2011, pending, the disclosure of which is incorporated by reference.

Referring next to FIG. 2B, the therapy lead 13 delivers an electrical signal from the neurostimulator 12 to the vagus nerve 15, 16 via the helical electrodes 14. On a proximal end, the therapy lead 13 has a lead connector 27 that transitions an insulated electrical lead body to a metal connector pin 28. During implantation, the connector pin 28 is guided through the receptacle 25 into the header 24 and securely fastened in place using the set screws 26 to electrically couple the therapy lead 13 to the neurostimulator 12. On a distal end, the therapy lead 13 terminates with the helical electrode 14, which bifurcates into a pair of anodic and cathodic electrodes 62 (as further described below with reference to FIG. 4). In one embodiment, the lead connector 27 is manufactured using silicone and the connector pin 28 is made of stainless steel, although other suitable materials could be used, as well. The insulated lead body 13 utilizes a silicone-insulated alloy conductor material.

Preferably, the helical electrodes 14 are placed over the cervical vagus nerve 15, 16 at the location below where the superior and inferior cardiac branches separate from the cervical vagus nerve. In alternative embodiments, the helical electrodes may be placed at a location above where one or both of the superior and inferior cardiac branches separate from the cervical vagus nerve. In one embodiment, the helical electrodes 14 are positioned over the patient's vagus nerve oriented with the end of the helical electrodes 14 facing the patient's head. At the distal end, the insulated electrical lead body 13 is bifurcated into a pair of lead bodies that are connected to a pair of electrodes proper. The polarity of the electrodes could be configured into a monopolar cathode, a proximal anode and a distal cathode, or a proximal cathode and a distal anode.

Therapeutically, the VNS is delivered as a cardiac cycle-independent maintenance dose through continuously-cycling, intermittent and periodic cycles of electrical pulses and rest (inhibition), which are system output behaviors that are pre-specified within the neurostimulator 12 through the stored stimulation parameters and timing cycles implemented in firmware and executed by the microprocessor. The neurostimulator 12 can operate either with or without an integrated heart rate sensor, such as respectively described in commonly-assigned U.S. Patent application, entitled "Implantable Device for Providing Electrical Stimulation of Cervical Vagus Nerves for Treatment of Chronic Cardiac Dysfunction with Leadless Heart Rate Monitoring," Ser. No. 13/314,126, filed on Dec. 7, 2011, pending, and U.S. Patent application, entitled "Implantable Device for Providing Electrical Stimulation of Cervical Vagus Nerves for Treatment of Chronic Cardiac Dysfunction," Ser. No. 13/314,119, filed on Dec. 7, 2011, pending, the disclosures of which are hereby incorporated by reference herein in their entirety. Additionally, where an integrated leadless heart rate monitor is available, the neurostimulator 12 can provide autonomic cardiovascular drive evaluation and self-controlled titration, such as respectively described in commonly-assigned U.S. Patent application, entitled "Implantable Device for Evaluating Autonomic Cardiovascular Drive in a Patient Suffering from Chronic Cardiac Dysfunction," Ser. No. 13/314,133, filed on Dec. 7, 2011, pending, and U.S. Patent application, entitled "Implantable Device for Providing Electrical Stimulation of Cervical Vagus Nerves for Treatment of Chronic Cardiac Dysfunction with Bounded Titration," Ser. No. 13/314,135, filed on Dec. 7, 2011, pending, the disclosures of which are hereby incorporated by reference herein in their entirety.

Figure 3:
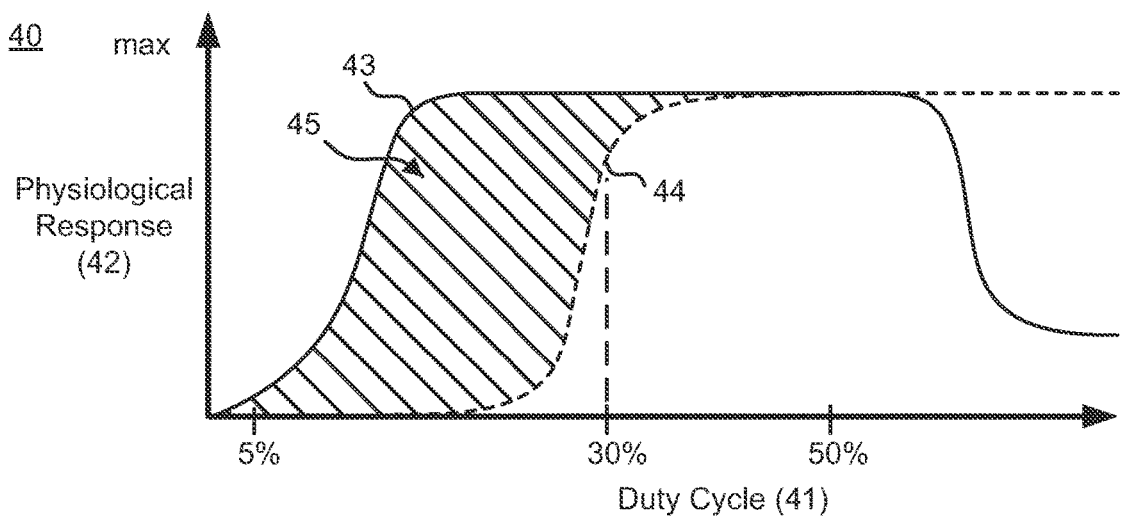
FIG. 3 is a graph showing, by way of example, the relationship between the targeted therapeutic efficacy and the extent of potential side effects resulting from use of the implantable neurostimulator of FIG. 1.

VNS is delivered as a heart failure therapy independent of cardiac cycle and in a maintenance dose low enough to not elicit side-effects, such as cardiac arrhythmias. The VNS can be delivered with a periodic duty cycle in the range of 2% to 89% with a preferred range of around 4% to 36% that is delivered as a low intensity maintenance dose. The selection of duty cycle is a tradeoff between competing medical considerations. FIG. 3 is a graph 40 showing, by way of example, the relationship between the targeted therapeutic efficacy 43 and the extent of potential side effects 44 resulting from use of the implantable neurostimulator 12 of FIG. 1. The x-axis represents the duty cycle 41. The duty cycle is determined by dividing the stimulation time by the sum of the ON and OFF times of the neurostimulator 12. However, the stimulation time may also need to include ramp-up time and ramp-down time, where the stimulation frequency exceeds a minimum threshold (as further described below with reference to FIG. 5). The y-axis represents physiological response 42 to VNS therapy. The physiological response 42 can be expressed quantitatively for a given duty cycle 41 as a function of the targeted therapeutic efficacy 43 and the extent of potential side effects 44, as described infra. The maximum level of physiological response 42 ("max") signifies the highest point of targeted therapeutic efficacy 43 or potential side effects 44.

Targeted therapeutic efficacy 43 and the extent of potential side effects 44 can be expressed as functions of duty cycle 41 and physiological response 42. The targeted therapeutic efficacy 43 represents the intended effectiveness of VNS in provoking a beneficial physiological response for a given duty cycle and can be quantified by assigning values to the various acute and chronic factors that contribute to the physiological response 42 of the patient 10 due to the delivery of therapeutic VNS. Acute factors that contribute to the targeted therapeutic efficacy 43 include increase in heart rate variability and coronary flow, reduction in cardiac workload through vasodilation, and improvement in left ventricular relaxation. Chronic factors that contribute to the targeted therapeutic efficacy 43 include decreased parasympathetic activation and increased sympathetic activation, as well as decreased negative cytokine production, increased baroreflex sensitivity, increased respiratory gas exchange efficiency, favorable gene expression, renin-angiotensin-aldosterone system down-regulation, anti-arrhythmic, anti-apoptotic, and ectopy-reducing anti-inflammatory effects. These contributing factors can be combined in any manner to express the relative level of targeted therapeutic efficacy 43, including weighting particular effects more heavily than others or applying statistical or numeric functions based directly on or derived from observed physiological changes. Empirically, targeted therapeutic efficacy 43 steeply increases beginning at around a 5% duty cycle, and levels off in a plateau near the maximum level of physiological response at around a 30% duty cycle. Thereafter, targeted therapeutic efficacy 43 begins decreasing at around a 50% duty cycle and continues in a plateau near a 25% physiological response through the maximum 100% duty cycle.

The extent of potential side effects 44 represents the occurrence of a possible physiological effect, either adverse, such as bradycardia, or therapeutic, that is secondary to the benefit intended, which presents in the patient 10 in response to VNS and can be quantified by assigning values to the physiological effects presented due to the delivery of therapeutic VNS. The degree to which a patient 10 may be prone to exhibit side effects depends in large part upon the patient's condition, including degree of cardiac dysfunction, both acute and chronic, any comobidities, prior heart problems, family history, general health, and similar considerations. As well, the type and severity of a side effect is patient-dependent. For VNS in general, the more common surgical- and stimulation-related adverse side effects include infection, asystole, bradycardia, syncope, abnormal thinking, aspiration pneumonia, device site reaction, acute renal failure, nerve paralysis, hypesthesia, facial paresis, vocal cord paralysis, facial paralysis, hemidiaphragm paralysis, recurrent laryngeal injury, urinary retention, and low grade fever. The more common non-adverse side effects include hoarseness, voice alteration, increased coughing, pharyngitis, paresthesia, dyspnea, dyspepsia, nausea, and laryngismus. Less common side effects, including adverse events, include ataxia, hypesthesia, increase coughing, insomnia, muscle movement or twitching associated with stimulation, nausea, pain, paresthesia, pharyngitis, vomiting, aspiration, blood clotting, choking sensation, nerve damage, vasculature damage, device migration or extrusion, dizziness, dysphagia, duodenal or gastric ulcer, ear pain, face flushing, facial paralysis or paresis, implant rejection, fibrous tissue formation, fluid pocket formation, hiccupping, incision site pain, irritability, laryngeal irritation, hemidiaphragm paralysis, vocal cord paralysis, muscle pain, neck pain, painful or irregular stimulation, seroma, skin or tissue reaction, stomach discomfort, tinnitus, tooth pain, unusual scarring at incision site, vagus nerve paralysis, weight change, worsening of asthma or bronchitis. These quantified physiological effects can be combined in any manner to express the relative level of extent of potential side effects 44, including weighting particular effects more heavily than others or applying statistical or numeric functions based directly on or derived from observed physiological changes. Empirically, the extent of potential side effects 44 is initially low until around a 25% duty cycle, at which point the potential begins to steeply increase. The extent of potential side effects 44 levels off in a plateau near the maximum level of physiological response at around a 50% duty cycle through the maximum 100% duty cycle.

Figure 4:
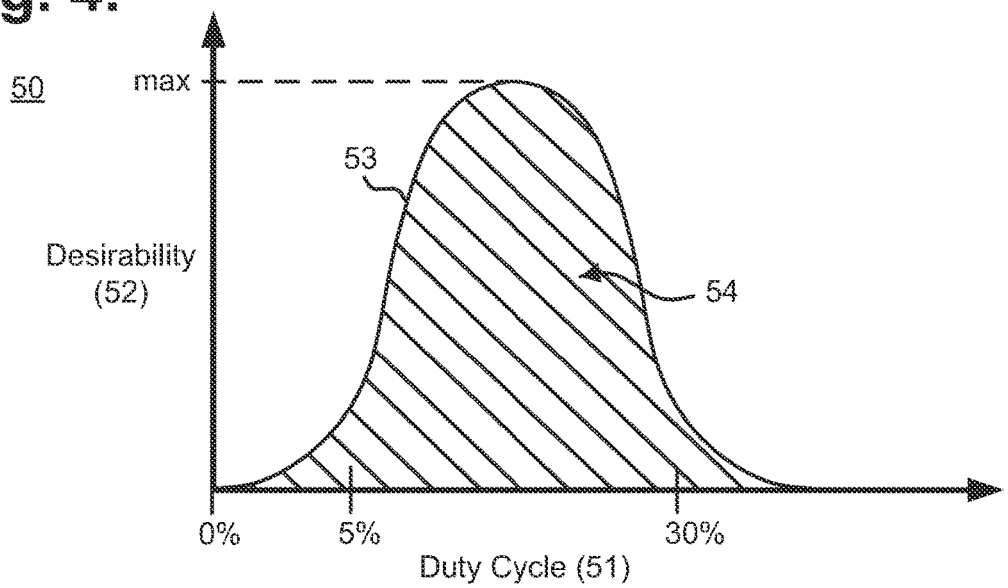
FIG. 4 is a graph showing, by way of example, the optimal duty cycle range based on the intersection depicted in FIG. 3.

The intersection 45 of the targeted therapeutic efficacy 43 and the extent of potential side effects 44 represents one optimal duty cycle range for VNS. FIG. 4 is a graph 50 showing, by way of example, the optimal duty cycle range 53 based on the intersection 45 depicted in FIG. 3. The x-axis represents the duty cycle 51 as a percentage of stimulation time over inhibition time. The y-axis represents the desirability 52 of operating the neurostimulator 12 at a given duty cycle 51. The optimal duty range 53 is a function 54 of the intersection 44 of the targeted therapeutic efficacy 43 and the extent of potential side effects 44. The desirability 52 can be expressed quantitatively for a given duty cycle 51 as a function of the values of the targeted therapeutic efficacy 43 and the extent of potential side effects 44 at their point of intersection in the graph 40 of FIG. 3. The maximum level of desirability 52 ("max") signifies a tradeoff that occurs at the point of highest targeted therapeutic efficacy 43 in light of lowest potential side effects 44 and that point will typically be found within the range of a 5% to 30% duty cycle 51. Other expressions of duty cycles and related factors are possible.

Figure 5:
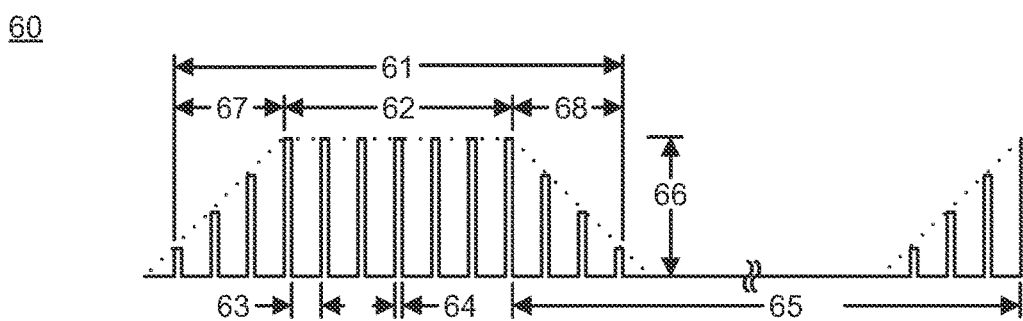
FIG. 5 is a timing diagram showing, by way of example, a stimulation cycle and an inhibition cycle of VNS as provided by implantable neurostimulator of FIG. 1.

VNS is delivered in a low level maintenance dose that uses alternating cycles of stimuli application (ON) and stimuli inhibition (OFF) that are tuned to both efferently activate the heart's intrinsic nervous system and heart tissue and afferently activate the patient's central reflexes. FIG. 5 is a timing diagram showing, by way of example, a stimulation cycle and an inhibition cycle of VNS 60 as provided by implantable neurostimulator 12 of FIG. 1. The stimulation parameters enable the electrical stimulation pulse output by the neurostimulator 12 to be varied by both amplitude (output current 66) and duration (pulse width 64). The number of output pulses delivered per second determines the signal frequency 63. In one embodiment, a pulse width in the range of 100 to 250 μsec delivers between 0.02 and 50 mA of output current at a signal frequency of about 20 Hz, although other therapeutic values could be used as appropriate.

In the simplest case, the stimulation time is the time period during which the neurostimulator 12 is ON and delivering pulses of stimulation. The OFF time 65 is always the time period occurring in-between stimulation times 61 during which the neurostimulator 12 is OFF and inhibited from delivering stimulation. In one embodiment, the neurostimulator 12 implements a ramp-up time 67 and a ramp-down time 68 that respectively precede and follow the ON time 62 during which the neurostimulator 12 is ON and delivering pulses of stimulation at the full output current 66. The ramp-up time 67 and ramp-down time 68 are used when the stimulation frequency is at least 10 Hz, although other minimum thresholds could be used, and both times last two seconds, although other time periods could also be used. The ramp-up time 67 and ramp-down time 68 allow the strength of the output current 66 of each output pulse to be gradually increased and decreased, thereby avoiding unnecessary trauma to the vagus nerve due to sudden delivery or inhibition of stimulation at full strength.

Therapeutic VNS can potentially exacerbate pathological bradycardia. The increased parasympathetic activity that occurs in response to the triggering of CHF compensatory mechanisms increases the risk of bradycardia. VNS therapy can be suspended upon the occurrence of bradycardia, after which therapy only resumes if bradycardia does not recur. FIG. 6 is a flow diagram showing an implantable neurostimulator-implemented method for managing bradycardia through vagus nerve stimulation 70, in accordance with one embodiment. The method is implemented on the stimulation device 11, the operation of which is parametrically defined through stored stimulation parameters and timing cycles.

Preliminarily, an implantable neurostimulator 12, which includes a pulse generator 11, a nerve stimulation therapy lead 13, and a pair of helical electrodes 14, is provided (step 71). In an alternative embodiment, electrodes may be implanted with no implanted neurostimulator or leads. Power may be provided to the electrodes from an external power source and neurostimulator through wireless RF or inductive coupling. Such an embodiment may result in less surgical time and trauma to the patient. Referring back to FIG. 6, the pulse generator 11 delivers electrical therapeutic stimulation to the cervical vagus nerve of a patient 10 in both afferent and efferent directions on either the left or right vagus nerve 15, 16. The pulse generator stores an operating mode (step 72) that parametrically defines a low level maintenance dose of the stimulation, which is tuned, as described supra, to restore cardiac autonomic balance through continuously-cycling, intermittent and periodic electrical pulses.

Therapeutic VNS is delivered to the vagus nerve independent of cardiac cycle (step 73). During therapy delivery, the patient's physiology is checked for bradycardia (step 74), as further described below with reference to FIGS. 7 and 8. If a monitored condition of the patient is indicative of bradycardia, that is, the patient's physiology indicates the onset or presence of bradycardia (step 75), the delivery of the maintenance dose is suspended. In the context of therapeutic VNS delivery, however, bradycardia that presents recurrently following the resumption of therapy (step 76) is suspended and provisionally resumed by applying a progressive therapy delivery resumption protocol (step 77), which incrementally increases duty cycle and delay, as further described below with reference to FIG. 9. Otherwise, if bradycardia presents independently of a recent resumption of therapy delivery and is therefore not recurrent (step 76), VNS delivery is temporarily suspended (step 78), after which time therapy delivery resumes (step 79). The period of suspension will be between 15 and 30 minutes, or as appropriate to the situation. In one embodiment, the duration of suspension may be determined based on continued monitoring of the patient's heart rate or sinus rhythm, including the type of bradycardia or arrhythmia detected.

The onset or presence of pathological bradycardia can be determined by heart rate or normal sinus rhythm through an endocardial electrogram. Other physiological measures are possible. For instance, sick sinus bradycardia, a form of atrial bradycardia, presents with a resting heart rate below 60 bpm, while atrioventricular nodal bradycardia presents with a normal QRS complex accompanied by an inverted P wave. Conversely, ventricular bradycardia presents with a wide QRS complex and heart rate between 20 and 40 bpm, while junctional ventricular bradycardia presents with a narrow QRS complex and heart rate between 40 and 60 bpm. Once suspended, VNS delivery is only continually resumed if, during post-suspension monitoring, bradycardia is not found to recur as a result of VNS resumption (step 77), the delivery of the maintenance dose is resumed (step 73). Otherwise, therapy remains suspended.

Figure 7:
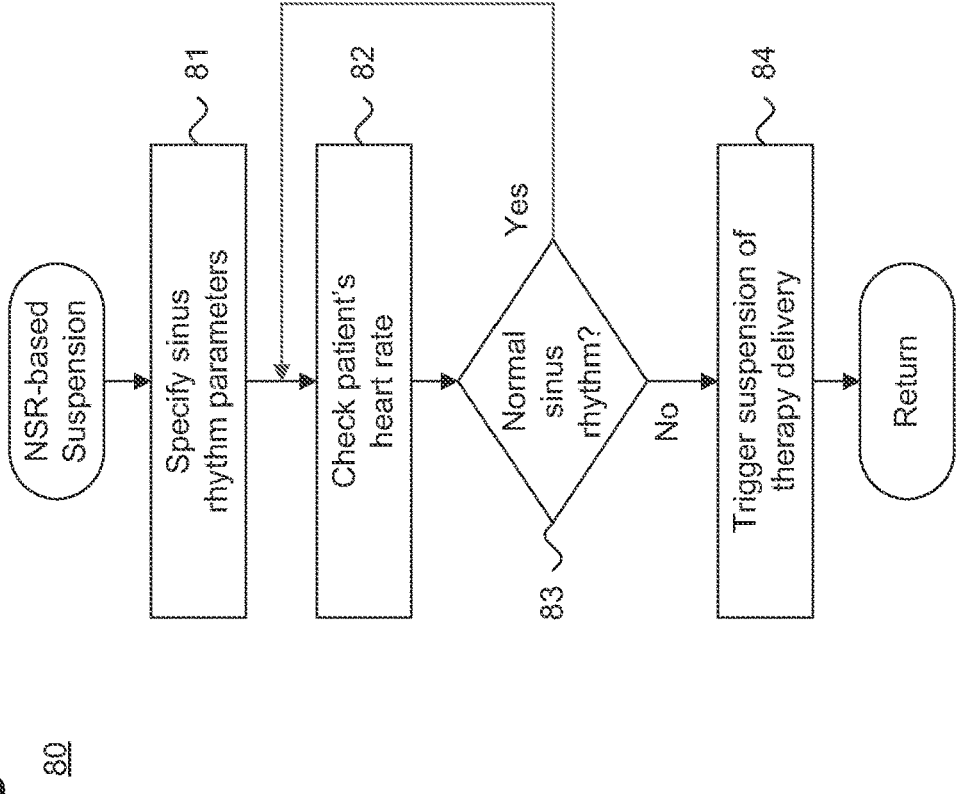
FIG. 7 is a flow diagram showing a routine for suspending therapy delivery based on normal sinus rhythm for use with the method of FIG. 6.

The onset or presence of bradycardia can be identified by evaluating sinus rhythm or heart rate through a physiological sensor. FIG. 7 is a flow diagram showing a routine for suspending therapy delivery based on normal sinus rhythm 80 for use with the method 70 of FIG. 6. Normal sinus rhythm is a state of normal heart rate and rhythm. Parameters that define normal sinus rhythm are specified (step 81), which can be parametrically programmed into the implantable neurostimulator 12. During VNS therapy delivery, the patient's heart rate is monitored (step 82) using, for instance, a single block electrode on the vagus nerve and the neurostimulator's header 24, which respectively form a sinus rhythm sensor. In a further embodiment, the neurostimulator 12 could be augmented with an endocardial sensing electrode. If the sinus rhythm is not normal (step 83), for example, the P wave is inverted or the QRS complex is too wide or narrow, bradycardia has onset or exists and therapy delivery is suspended (step 84).

Figure 8:
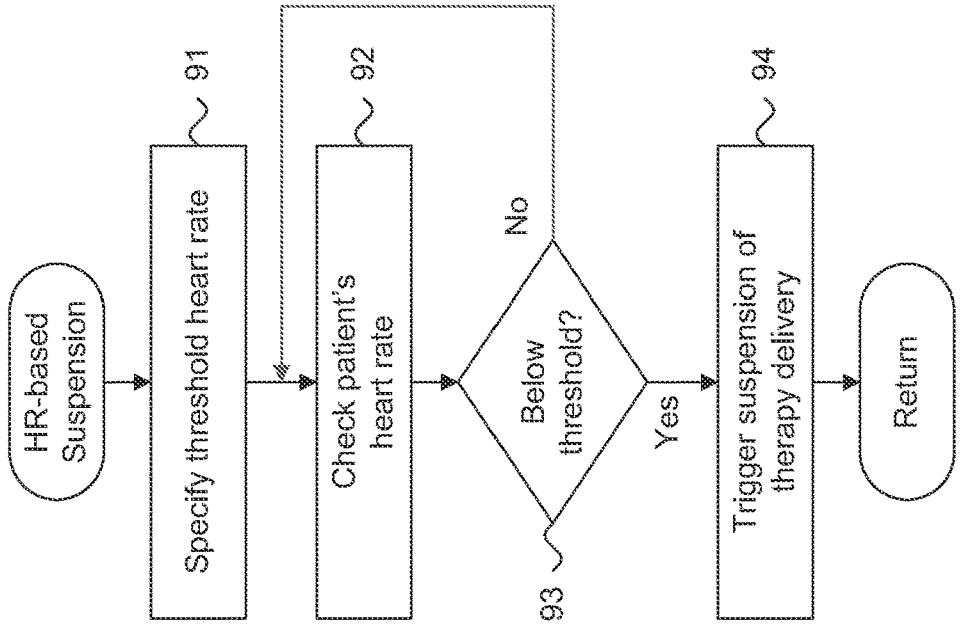
FIG. 8 is a flow diagram showing an alternative routine for suspending therapy delivery based on heart rate for use with the method of FIG. 6, in accordance with a further embodiment.

Alternatively, heart rate can be monitored to sense bradycardia. FIG. 8 is a flow diagram showing an alternative (or additional) routine for suspending therapy delivery based on heart rate 90 for use with the method 70 of FIG. 6, in accordance with a further embodiment. The implantable neurostimulator 12 includes a leadless heart rate sensor, such as available with a VNS Therapy AspireSR Model 106 pulse generator, manufactured and sold by Cyberonics, Inc., Houston, TX A minimum acceptable threshold heart rate, such as 50 bpm, is specified (step 91). During VNS therapy delivery, the patient's heart rate is checked (step 92). If the heart rate falls below the threshold (step 93), bradycardia has onset or exists and therapy delivery is suspended (step 94).

Figure 9:
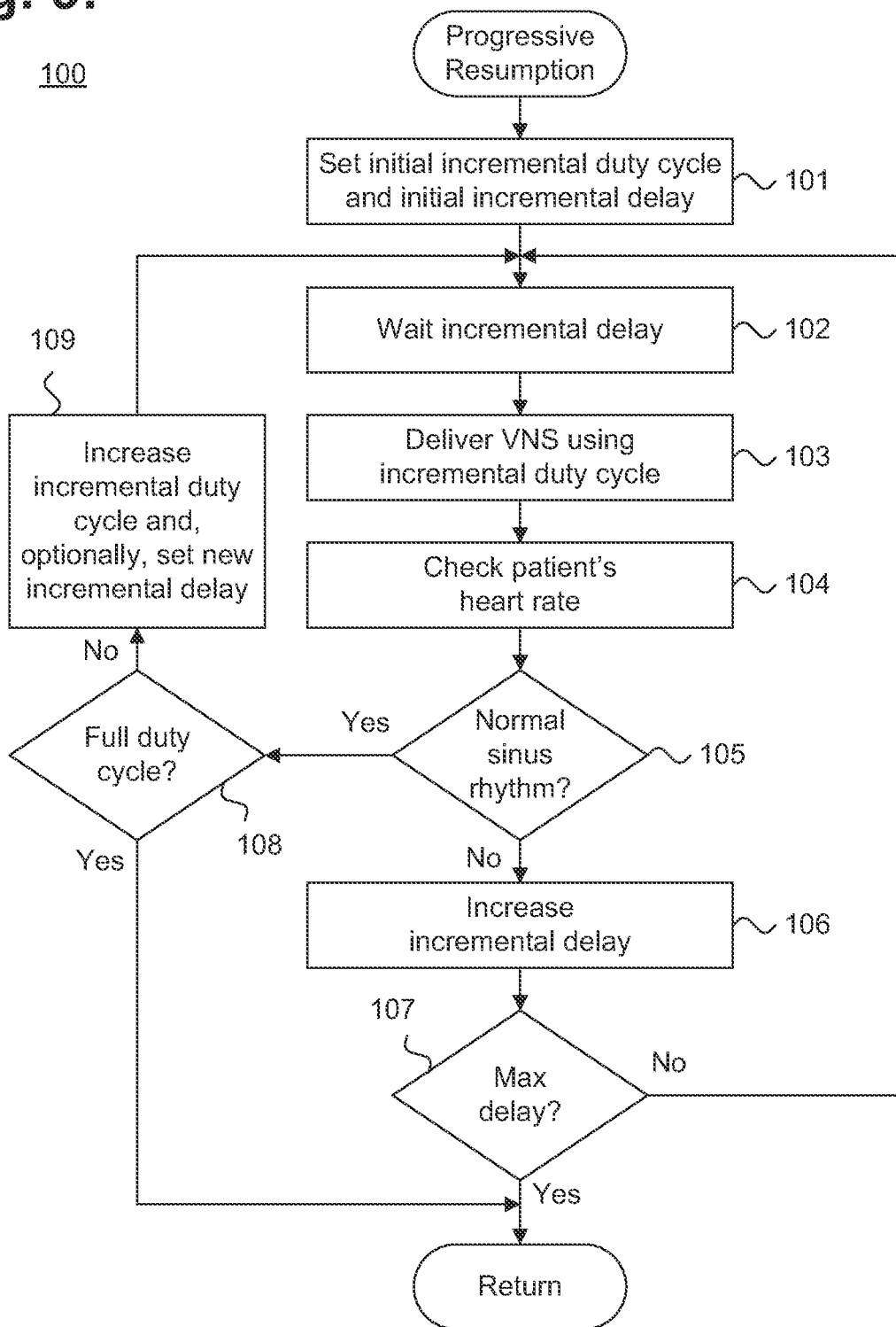
FIG. 9 is a flow diagram showing a routine for progressively resuming therapy delivery for use with the method of FIG. 6.

Following the resumption of therapy, VNS will not be continually resumed at the normal full duty cycle if bradycardia recurs to counter the chance that the VNS is either aggravating or causing the bradycardia. A progressive therapy delivery resumption protocol is instead used to gradually resume VNS therapy delivery. FIG. 9 is a flow diagram showing a routine for progressively resuming therapy delivery 100 for use with the method 70 of FIG. 6. The protocol progressively adapts to the recurrence of bradycardia in the patient 11. Temporally, the protocol uses an exponential back-off delay to increase the amount of time lapsing between attempts at resuming VNS therapy. Therapeutically, the protocol steadily increases the duty cycle of VNS delivery once bradycardia appears to no longer be recurring.

Initially, an initial incremental partial duty cycle and initial incremental delay are set (step 101), which can be parametrically programmed into the implantable neurostimulator 12. In one embodiment, the initial incremental duty cycle begins with a two-second pulse train and an initial incremental delay of ten minutes, although other initial incremental duty cycles and delays could be used. VNS therapy is suspended for the period of the initial incremental delay (step 102), after which VNS stimulation is delivered at the initial incremental duty cycle (step 103). Monitoring of the patient's physiology is resumed and the patient's heart rate is periodically checked (step 104) using, for instance, a block electrode on the vagus nerve or an endocardial sensing electrode and, if the patient's condition remains clear of indications of bradycardia, the incremental duty cycle is gradually increased with each successive heart rate check until the full maintenance duty cycle is reached.

The amount of time needed before bradycardia terminates varies and does not generally follow a temporally linear, and therefore predictable, curve from onset to termination. As well, regularly monitoring the patient's physiology throughout the period of therapy suspension can needlessly consume pulse generator 11 resources, while resuming VNS therapy after a fixed period of delay can expose the patient to potentially harmful VNS too soon. Consequently, the pulse generator 11 applies a form of exponential back-off delay algorithm between attempts at resuming VNS delivery. If, after the initial incremental period of delay, the sinus rhythm is still abnormal (step 105), the pulse generator 11 increases the duration of the incremental delay (step 106).

Figure 10:
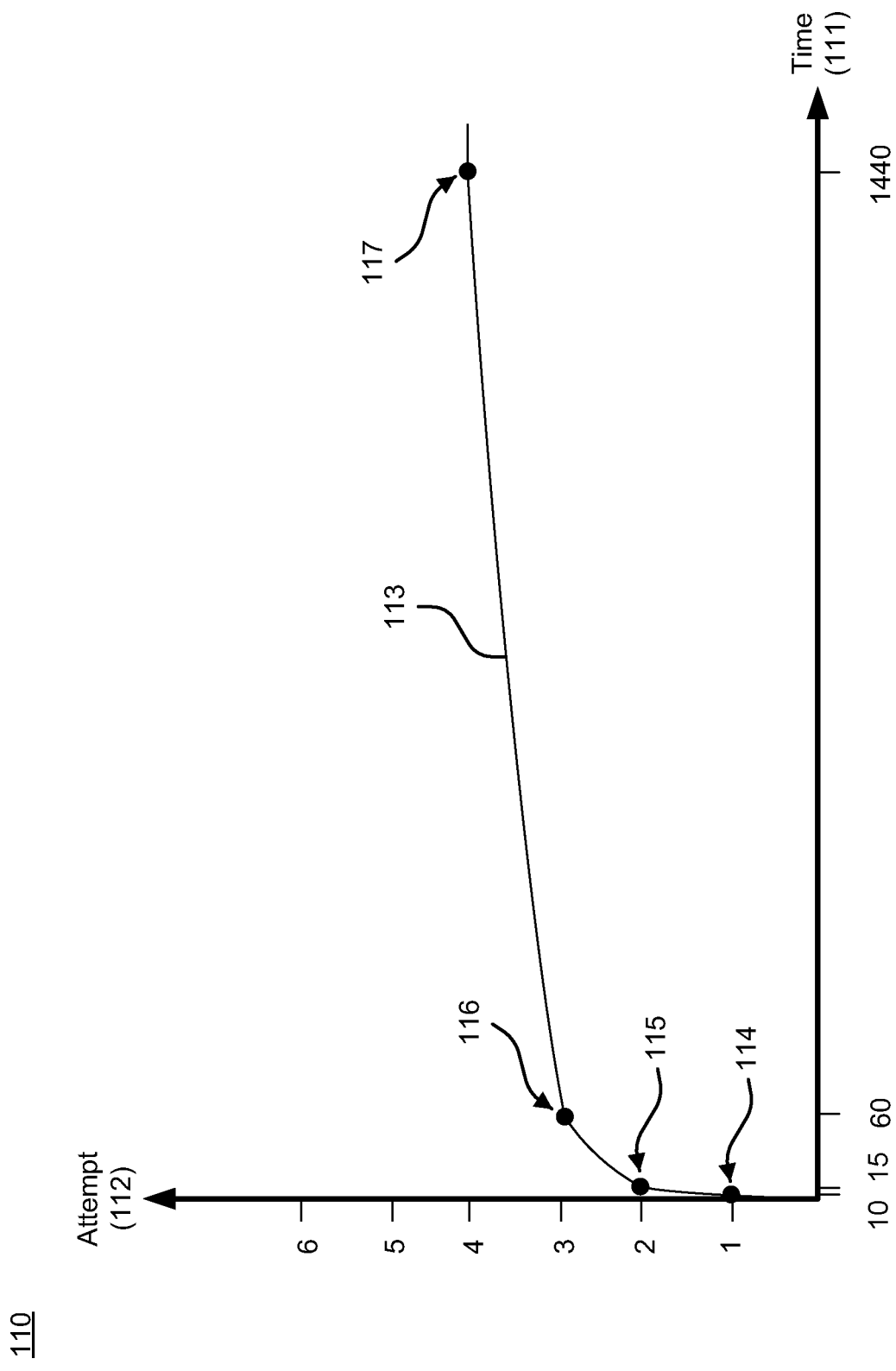
FIG. 10 is a timing diagram showing, by way of example, an exponential back-off delay as used in the routine of FIG. 9.

The incremental waiting period generated by the exponential back-off delay algorithm can be parametrically adjusted. FIG. 10 is a timing diagram 110 showing, by way of example, an exponential back-off delay 113 as used in the routine 100 of FIG. 9. The x-axis 111 represents time in minutes, although other time increments could be used. The y-axis 112 represents the number of attempts at resuming therapy delivery, that is, the number of times that the patient's physiology is checked. Here, the pulse generator 11 waits an initial incremental delay of 10 minutes (point 114) before delivering VNS at the initial incremental duty cycle and checking the patient's physiology for the first time, followed by increasingly larger delays of 15 minutes (point 115), one hour (point 116), 24 hours (point 117), and three days (not shown), assuming continuing bradycardia, before suspending VNS therapy indefinitely once the maximum delay has been reached. Other forms of incrementally increasing the delay could be used, including binary exponential, truncated binary exponential and stochastic back-off algorithms.

Referring back to FIG. 9, VNS therapy is again suspended for the period of the increased incremental delay (step 102), after which VNS stimulation is delivered (step 103) and the patient's heart rate checked (step 104). The cycle of increasing the incremental delay, delivering VNS and checking the patient's heart rate (steps 102-107) is repeated, until either normal sinus rhythm is restored (step 105) or the maximum delay has been reached (step 107), after which VNS therapy is suspended indefinitely.

Once normal sinus rhythm has successfully been restored (step 105), the duty cycle is then also incrementally increased (step 109) until the full duty cycle has been reached (step 108). Optionally, a new period of incremental delay can also be set (step 109). VNS therapy is again suspended for the period of the incremental delay (step 102), after which VNS stimulation is delivered at the incrementally increased duty cycle (step 103) and the patient's heart rate checked (step 104). The cycle of increasing the incremental duty cycle, delivering VNS and checking the patient's heart rate (steps 102-105, 108 and 109) is repeated, until the full duty cycle has been reached (step 108) or abnormal sinus rhythm that indicates a recurrence of bradycardia is encountered (step 105), after which VNS therapy is suspended once more using the next period of incremental delay at which the protocol left off.

In still further embodiments, both the suspension and resumption of therapy delivery can be titrated to gradually withdraw or introduce VNS. As well, therapy delivery can be manually suspended by providing the neurostimulator 12 with a magnetically-actuated reed switch that suspends therapy delivery in response to a remotely applied magnetic signal.

While the invention has been particularly shown and described as referenced to the embodiments thereof, those skilled in the art will understand that the foregoing and other changes in form and detail may be made therein without departing from the spirit and scope.

What is claimed is:

1. A method for managing bradycardia, the method comprising:
   delivering stimulation to a vagus nerve of a patient at a full duty cycle;
   monitoring the patient's physiology via a physiological sensor;

upon sensing a condition indicative of bradycardia, suspending the delivery of the stimulation to the vagus nerve for a first period of delay;
upon expiry of the first period of delay:
resuming the delivery of the stimulation to the vagus nerve at a partial duty cycle;
checking the patient's physiology via the physiological sensor;
upon sensing, subsequent to the first period of delay, a condition indicative of a recurrence of bradycardia, re-suspending the delivery of the stimulation to the vagus nerve for a second period of delay, the second period of delay being longer than the first period of delay; and
upon sensing, subsequent to the second period of delay, a condition indicative of an absence or termination of the bradycardia, gradually increasing the partial duty cycle of the stimulation from the partial duty cycle toward the full duty cycle.

2. The method of claim 1, further comprising:
upon expiry of the second period of delay:
resuming the delivery of the stimulation to the vagus nerve; and
checking the patient's physiology via the physiological sensor; and
upon sensing, subsequent to the second period of delay, a condition indicative of another recurrence of bradycardia, re-suspending the delivery of the stimulation to the vagus nerve for a third period of delay, the third period of delay being longer than the second period of delay.

3. The method of claim 2, wherein a first difference between the third period of delay and the second period of delay is larger than a second difference between the second period of delay and the first period of delay.

4. The method of claim 1, further comprising:
upon sensing consecutive conditions indicative of recurrences of bradycardia subsequent to corresponding consecutive periods of delay, suspending the delivery of the stimulation to the vagus nerve for exponentially longer periods of delay.

5. The method of claim 4, further comprising:
upon reaching a programmed maximum delay, terminating the delivery of the stimulation to the vagus nerve.

6. The method of claim 1, wherein the condition indicative of bradycardia is sensed based on at least one of abnormal sinus rhythm and heart rate falling below a threshold.

7. The method of claim 1, wherein the partial duty cycle of the stimulation is gradually increased while continually monitoring the patient's physiology until one of the full duty cycle is reached or another condition indicative of bradycardia is sensed.

8. A vagus nerve stimulation (VNS) device comprising:
a physiological sensor configured to monitor a patient's physiology;
an implantable neurostimulator configured to deliver stimulation to a vagus nerve of the patient via at least one stimulation electrode; and
a processor and a memory storing stimulation parameters executable by the processor to:
deliver stimulation to the vagus nerve of the patient at a full duty cycle;
monitor the patient's physiology via the physiological sensor;
upon sensing a condition indicative of bradycardia, suspend the delivery of the stimulation to the vagus nerve for a first period of delay;
upon expiry of the first period of delay:
resume the delivery of the stimulation to the vagus nerve at a partial duty cycle; and
check the patient's physiology via the physiological sensor; and
upon sensing, subsequent to the first period of delay, a condition indicative of a recurrence of bradycardia, re-suspending the delivery of the stimulation to the vagus nerve for a second period of delay, the second period of delay being longer than the first period of delay
upon sensing, subsequent to the second period of delay, a condition indicative of an absence or termination of the bradycardia, gradually increasing the partial duty cycle of the stimulation from the partial duty cycle toward the full duty cycle.

9. The VNS device of claim 8, wherein the stimulation parameters are further executable by the processor to:
upon expiry of the second period of delay:
resume the delivery of the stimulation to the vagus nerve; and
check the patient's physiology via the physiological sensor; and
upon sensing, subsequent to the second period of delay, a condition indicative of another recurrence of bradycardia, re-suspend the delivery of the stimulation to the vagus nerve for a third period of delay, the third period of delay being longer than the second period of delay.

10. The VNS device of claim 9, wherein a first difference between the third period of delay and the second period of delay is larger than a second difference between the second period of delay and the first period of delay.

11. The VNS device of claim 8, wherein the stimulation parameters are further executable by the processor to:
upon sensing consecutive conditions indicative of recurrences of bradycardia subsequent to corresponding consecutive periods of delay, suspend the delivery of the stimulation to the vagus nerve for exponentially longer periods of delay.

12. The VNS device of claim 11, wherein the stimulation parameters are further executable by the processor to:
upon reaching a programmed maximum delay, terminate the delivery of the stimulation to the vagus nerve.

13. The VNS device of claim 8, wherein the condition indicative of bradycardia is sensed based on at least one of abnormal sinus rhythm and heart rate falling below a threshold.

14. The VNS device of claim 8, wherein the partial duty cycle of the stimulation is gradually increased while continually monitoring the patient's physiology until one of the full duty cycle is reached or-another condition indicative of bradycardia is sensed.

15. A non-transitory computer readable storage medium storing stimulation parameters executable by a processor to:
deliver stimulation to a vagus nerve of a patient at a full duty cycle;
monitoring the patient's physiology via a physiological sensor;
upon sensing a condition indicative of bradycardia, suspend the delivery of the stimulation to the vagus nerve for a first period of delay;
upon expiry of the first period of delay:
resume the delivery of the stimulation to the vagus nerve at a partial duty cycle;

check the patient's physiology via the physiological sensor; and upon sensing, subsequent to the first period of delay, a condition indicative of a recurrence of bradycardia, re-suspending the delivery of the stimulation to the vagus nerve for a second period of delay, the second period of delay being longer than the first period of delay; and upon sensing, subsequent to the second period of delay, a condition indicative of an absence or termination of the bradycardia, gradually increasing the partial duty cycle of the stimulation from the partial duty cycle toward the full duty cycle.

16. The non-transitory computer readable storage medium of claim 15, wherein the stimulation parameters are further executable by the processor to:

upon expiry of the second period of delay:
resume the delivery of the stimulation to the vagus nerve; and
check the patient's physiology via the physiological sensor; and upon sensing, subsequent to the second period of delay, a condition indicative of another recurrence of bradycardia, re-suspend the delivery of the stimulation to the vagus nerve for a third period of delay, the third period of delay being longer than the second period of delay.

17. The non-transitory computer readable storage medium of claim 16, wherein a first difference between the third period of delay and the second period of delay is larger than a second difference between the second period of delay and the first period of delay.

18. The non-transitory computer readable storage medium of claim 15, wherein the stimulation parameters are further executable by the processor to:

upon sensing consecutive conditions indicative of recurrences of bradycardia subsequent to corresponding consecutive periods of delay, suspend the delivery of the stimulation to the vagus nerve for exponentially longer periods of delay.

* * * * *